US010426609B2

(12) United States Patent
Edelman et al.

(10) Patent No.: US 10,426,609 B2
(45) Date of Patent: Oct. 1, 2019

(54) FIBER REINFORCED PROSTHETIC HEART VALVE HAVING UNDULATING FIBERS

(71) Applicant: Boston Scientific SciMed, Inc., Maple Grove, MN (US)

(72) Inventors: Peter G. Edelman, Maple Grove, MN (US); Joseph Thomas Delaney, Jr., Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 334 days.

(21) Appl. No.: 15/082,239

(22) Filed: Mar. 28, 2016

(65) Prior Publication Data

US 2016/0296325 A1 Oct. 13, 2016

Related U.S. Application Data

(60) Provisional application No. 62/145,382, filed on Apr. 9, 2015.

(51) Int. Cl.
| | | |
|---|---|---|
| *A61F 2/24* | (2006.01) | |
| *A61L 27/50* | (2006.01) | |
| *B29C 70/30* | (2006.01) | |
| *A61L 27/48* | (2006.01) | |
| *B29L 31/00* | (2006.01) | |

(52) U.S. Cl.
CPC .......... *A61F 2/2418* (2013.01); *A61F 2/2409* (2013.01); *A61F 2/2412* (2013.01); *A61F 2/2415* (2013.01); *A61L 27/48* (2013.01); *A61L 27/50* (2013.01); *A61L 27/507* (2013.01); *B29C 70/30* (2013.01); *A61F 2210/0071* (2013.01); *A61F 2210/0076* (2013.01); *A61F 2250/0018* (2013.01); *A61F 2250/0028* (2013.01); *B29K 2995/0046* (2013.01); *B29L 2031/7532* (2013.01)

(58) Field of Classification Search
None
See application file for complete search history.

(56) References Cited

U.S. PATENT DOCUMENTS

| | | |
|---|---|---|
| 4,016,714 A | 4/1977 | Crandall et al. |
| 4,340,091 A | 7/1982 | Davis et al. |
| 4,753,652 A | 6/1988 | Langer et al. |
| 5,296,292 A | 3/1994 | Butters |
| 5,674,286 A | 10/1997 | Alessio et al. |

(Continued)

FOREIGN PATENT DOCUMENTS

| | | |
|---|---|---|
| CN | 1449266 | 10/2003 |
| CN | 1874799 | 12/2006 |

(Continued)

OTHER PUBLICATIONS

"Decision of Final Rejection," for China Patent Application No. 201380044842.0, dated Apr. 7, 2017 (18 pages) with Summary.

(Continued)

*Primary Examiner* — Leslie Lopez
(74) *Attorney, Agent, or Firm* — Pauly, DeVries Smith & Deffner LLC

(57) ABSTRACT

A prosthetic heart valve includes a composite material that has a first plurality of fibers embedded in a polymer matrix. Each fiber can have a first extending direction and a plurality of undulations.

11 Claims, 6 Drawing Sheets

(56) References Cited

U.S. PATENT DOCUMENTS

| | | |
|---|---|---|
| 5,679,299 A | 10/1997 | Gilbert et al. |
| 5,688,597 A | 11/1997 | Kohno |
| 5,740,051 A | 4/1998 | Sanders, Jr. et al. |
| 6,165,215 A | 12/2000 | Rottenberg et al. |
| 6,726,715 B2 | 4/2004 | Sutherland |
| 6,953,332 B1 | 10/2005 | Kurk et al. |
| 7,335,264 B2 | 2/2008 | Austin et al. |
| 7,517,353 B2 | 4/2009 | Weber |
| 7,521,296 B2 | 4/2009 | Wood et al. |
| 7,615,335 B2 | 11/2009 | Shelnut et al. |
| 7,786,670 B2 | 8/2010 | Veres et al. |
| 7,988,900 B2 | 8/2011 | Beith et al. |
| 8,324,290 B2 | 12/2012 | Desai et al. |
| 8,361,144 B2 | 1/2013 | Fish et al. |
| 8,590,747 B2 | 11/2013 | Keller et al. |
| 8,845,580 B2 | 9/2014 | Gellman et al. |
| 8,864,816 B2 | 10/2014 | Flanagan et al. |
| 8,975,372 B2 | 3/2015 | Ju et al. |
| 9,056,006 B2 | 6/2015 | Edelman et al. |
| 9,074,318 B2 | 7/2015 | Chou et al. |
| 9,255,929 B2 | 2/2016 | Jiang et al. |
| 9,481,949 B2 | 11/2016 | Zhang et al. |
| 9,554,900 B2 | 1/2017 | Bruchman et al. |
| 9,737,400 B2 | 8/2017 | Fish et al. |
| 9,814,572 B2 | 11/2017 | Edelman et al. |
| 9,944,529 B2 | 4/2018 | Zhang et al. |
| 10,195,023 B2 | 2/2019 | Wrobel |
| 10,299,915 B2 | 5/2019 | Edelman et al. |
| 2001/0025196 A1 | 9/2001 | Chinn et al. |
| 2002/0082689 A1 | 6/2002 | Chinn et al. |
| 2003/0055496 A1 | 3/2003 | Cai et al. |
| 2003/0078652 A1* | 4/2003 | Sutherland ............ A61F 2/2412 623/2.12 |
| 2003/0097175 A1 | 5/2003 | O'connor et al. |
| 2003/0171802 A1 | 9/2003 | Wilder et al. |
| 2003/0183982 A1 | 10/2003 | Jansen et al. |
| 2004/0015233 A1 | 1/2004 | Jansen et al. |
| 2004/0022939 A1 | 2/2004 | Kim et al. |
| 2005/0228486 A1 | 10/2005 | Flagle et al. |
| 2006/0190074 A1 | 8/2006 | Hill et al. |
| 2007/0118210 A1 | 5/2007 | Pinchuk et al. |
| 2007/0144124 A1 | 6/2007 | Schewe et al. |
| 2007/0232169 A1 | 10/2007 | Strickler et al. |
| 2007/0254005 A1 | 11/2007 | Pathak et al. |
| 2008/0045420 A1 | 2/2008 | Karagianni et al. |
| 2009/0041978 A1* | 2/2009 | Sogard ............... A61F 2/2412 428/137 |
| 2009/0054969 A1 | 2/2009 | Salahieh et al. |
| 2009/0117334 A1 | 5/2009 | Sogard et al. |
| 2009/0149673 A1 | 6/2009 | Zhang et al. |
| 2009/0155335 A1 | 6/2009 | Oshaughnessey et al. |
| 2009/0324679 A1 | 12/2009 | Ippoliti et al. |
| 2010/0023104 A1 | 1/2010 | Desai et al. |
| 2010/0179298 A1 | 7/2010 | Faust et al. |
| 2010/0249022 A1 | 9/2010 | Li et al. |
| 2011/0022160 A1 | 1/2011 | Flanagan et al. |
| 2011/0208299 A1 | 8/2011 | Marissen et al. |
| 2011/0305898 A1 | 12/2011 | Zhang et al. |
| 2012/0258313 A1 | 10/2012 | Wen et al. |
| 2012/0290082 A1 | 11/2012 | Quint et al. |
| 2013/0150957 A1 | 6/2013 | Weber et al. |
| 2013/0211508 A1 | 8/2013 | Lane et al. |
| 2013/0274874 A1 | 10/2013 | Hammer et al. |
| 2014/0005771 A1 | 1/2014 | Braido et al. |
| 2014/0005772 A1 | 1/2014 | Edelman et al. |
| 2014/0018440 A1 | 1/2014 | Boden et al. |
| 2014/0088716 A1 | 3/2014 | Zubok et al. |
| 2014/0163671 A1 | 6/2014 | Bruchman et al. |
| 2014/0180402 A1 | 6/2014 | Bruchman et al. |
| 2014/0322512 A1 | 10/2014 | Pham et al. |
| 2015/0005869 A1 | 1/2015 | Soletti et al. |
| 2015/0182332 A1 | 7/2015 | Edelman et al. |
| 2015/0265392 A1 | 9/2015 | Flanagan et al. |
| 2016/0296322 A1 | 10/2016 | Edelman |
| 2016/0296323 A1 | 10/2016 | Wulfman et al. |
| 2017/0000610 A1 | 1/2017 | Eppihimer et al. |
| 2017/0014227 A1 | 1/2017 | Boden et al. |
| 2017/0071729 A1 | 3/2017 | Wrobel |
| 2017/0156854 A1 | 6/2017 | Hammer |
| 2017/0231758 A1 | 8/2017 | Bruchman et al. |
| 2017/0266350 A1 | 9/2017 | Jiang et al. |
| 2017/0333185 A1 | 11/2017 | Weber et al. |
| 2018/0049869 A1 | 2/2018 | Edelman et al. |
| 2018/0303972 A1 | 10/2018 | Delaney, Jr. et al. |

FOREIGN PATENT DOCUMENTS

| | | |
|---|---|---|
| CN | 101690683 | 4/2010 |
| CN | 103628147 | 3/2014 |
| JP | H0654868 | 3/1994 |
| WO | 0224119 | 3/2002 |
| WO | 02074201 | 9/2002 |
| WO | 2005039664 | 5/2005 |
| WO | 2006000763 | 1/2006 |
| WO | 2008097592 | 8/2008 |
| WO | 2009038761 | 3/2009 |
| WO | 2010020660 | 2/2010 |
| WO | 2010048281 | 4/2010 |
| WO | 2014008207 | 1/2014 |
| WO | 2014143866 | 9/2014 |
| WO | 2014149319 | 9/2014 |
| WO | 2016025945 | 2/2016 |
| WO | 2016164197 | 10/2016 |
| WO | 2016164209 | 10/2016 |
| WO | 2018200378 | 11/2016 |
| WO | 2017004035 | 1/2017 |
| WO | 2017011392 | 1/2017 |
| WO | 2017048575 | 3/2017 |
| WO | 2017200920 | 11/2017 |

OTHER PUBLICATIONS

"Non-Final Office Action," for U.S. Appl. No. 14/656,044 dated Mar. 17, 2017 (34 pages).

"Response to Non-Final Office Action," for U.S. Appl. No. 14/656,044 dated Mar. 17, 2017 and filed with the USPTO Jun. 8, 2017 (11 pages).

Aksoy, Ayse E. et al., "Surface Modification of Polyurethanes with Covalent Immobilization of Heparin," Macromolecular Symposia, vol. 269, Issue 1, pp. 145-153, Aug. 2008 (9 pages).

Alferiev, Ivan et al., "Prevention of polyurethane valve cusp calcification with covalently attached bisphosphonate diethylamino moieties," J Biomed Mater Res 66A: 385-395, 2003 (11 pages).

Athappan, Ganesh et al., "Influence of Transcatheter Aortic Valve Replacement Strategy and Valve Design on Stroke After Transcatheter Aortic Valve Replacement: A Meta-Analysis and Systematic Review of Literature," J Am Coll Cardiol. 2014;63(20):2101-2110 (10 pages).

Barkoula, Nektaria-Marianthi et al., "Processing of Single Polymer Composites Using the Concept of Constrained Fibers," Polymer Composites, 2005, 26: p. 114-120 (7 pages).

Bastiaansen, Cees W. et al., "Melting Behavior of Gelspun-Drawn Polyolefins," Makromol. Chem., Macromol. Symp., 1989. 28: p. 73-84 (12 pages).

Bates, Frank S. et al., "Multiblock Polymers: Panacea or Pandora's Box?," Science, 2012, 336:434-440 (7 pages).

Bernacca, Gillian M. et al., "Mechanical and morphological study of biostable polyurethane heart valve leaflets explanted from sheep," J Biomed Mater Res 61:138-145, 2002 (8 pages).

Bhattacharyya, D. et al., "Polyamide 6 single polymer composites," eXPRESS Polym. Lett., 2009. 3(8): p. 525-532 (8 pages).

Charles, Lyndon F. et al., "Self-reinforced composites of hydroxyapatite-coated PLLA fibers: fabrication and mechanical characterization," J. Mech. Behav. Biomed. Mater., 2013. 17: p. 269-277 (9 pages).

Claiborne, Thomas E. et al., "In Vitro Evaluation of a Novel Hemodynamically Optimized Trileaflet Polymeric Prosthetic Heart Valve," Journal of Biomechanical Engineering 2013, vol. 135 (8 pages).

(56) References Cited

OTHER PUBLICATIONS

De Yoreo, James J. et al., "Principles of Crystal Nucleation and Growth," Biomineralization, Mineral Soc. Am., Washington, DC, 2003, pp. 57-93 (37 pages).
Dencheva, Nadya et al., "Structure-properties relationship in single polymer composites based on polyamide 6 prepared by in-mold anionic polymerization," J. Mater. Sci., 2013. 48(20): p. 7260-7273 (14 pages).
Duhovic, Miro P. et al., "Polyamide 66 polymorphic single polymer composites," Open Macromol. J., 2009. 3: p. 37-40. (4 pages).
Fakirov, Stoyko "Nano- and Microfibrillar Single-Polymer Composites: A Review," Macromol. Mater. Eng., 2013. 298(1): p. 9-32 (24 pages).
Feng, Yakai et al., "Surface modification of polycarbonate urethane by covalent linkage of heparin with a PEG spacer," Transactions of Tianjin University, Feb. 2013, vol. 19, Issue 1, pp. 58-65 (8 pages).
File History for U.S. Appl. No. 13/932,968.
File History for U.S. Appl. No. 14/656,044.
"First Office Action," for Chinese Patent Application No. 201380044842.0 dated Dec. 18, 2015 (15 pages) with English Translation.
Généreux, Philippe et al., "Vascular Complications After Transcatheter Aortic Valve Replacement: Insights from the PARTNER Trial," J Am Coll Cardiol. 2012;60(12):1043-1052 (10 pages).
"Glycosaminoglycan," Wikipedia, posted on or before Oct. 16, 2004, retrieved Feb. 13, 2014, http://en.wikipedia.org/wiki/Glycosaminoglycan, 6 pages.
Gong, Ying et al., "Polyamide single polymer composites prepared via in situ anionic polymerization of ε-caprolactam," Composites, Part A, 2010. 41A(8): p. 1006-1011 (6 pages).
Gong, Ying et al., "Single polymer composites by partially melting recycled polyamide 6 fibers: preparation and characterization," J. Appl. Polym. Sci., 2010. 118(6): p. 3357-3363 (7 pages).
Goyal, R. K. et al., "High performance polymer composites on PEEK reinforced with aluminum oxide," J. Appl. Polym. Sci., 2006. 100(6): p. 4623-4631 (9 pages).
Han, Dong K. et al., "In vivo biostability and calcification-resistance of surface-modified PU-PEO-503," Journal of Biomedical Materials Research, vol. 27, 1063-1073, 1993 (11 pages).
Hine, P.J. et al., "High stiffness and high impact strength polymer composites by hot compaction of oriented fibers and tapes.," in Mechanical Properties of Polymers Based on Nanostructure and Morphology, CRC Press, 2005 (45 pages).
Hine, P.J. et al., "Hot compaction of woven nylon 6,6 multifilaments," J. Appl. Polym. Sci., 2006. 101(2): p. 991-997 (7 pages).
Hine, P.J. et al., "Hot Compaction of Woven Poly(ethylene terephthalate) Multifilaments," J. Appl. Polym. Sci., 2004. 91(4): p. 2223-2233 (11 pages).
Hine, P.J. et al., "Hybrid carbon fibre/nylon 12 single polymer composites," Composites Part A: Applied Science and Manufacturing 65 (2014) (17 pages).
"International Preliminary Report on Patentability," For International Application No. PCT/US2013/048976 dated Jan. 6, 2015 (9 pages).
"International Search Report & Written Opinion," for International Application No. PCT/US2013/048976 dated Nov. 19, 2013 (20 pages).
Jiang, Shaoyi et al., "Ultralow-Fouling, Functionalizable, and Hydrolyzable Zwitterionic Materials and Their Derivatives for Biological Applications," Adv Mater. Mar. 5, 2010;22(9):920-32 (13 pages).
Kaflon-Cohen, Estelle et al., "Microstructure and nematic transition in thermotropic liquid crystalline fibers and their single polymer composites," Polym. Adv. Technol., 2007. 18(9): p. 771-779 (9 pages).
Kang, Jungmee et al., "Polyisobutylene-Based Polyurethanes with Unprecedented Properties and How They Came About," Journal of Polymer Science Part A: Polymer Chemistry, 2011. 49(18): p. 3891-3904 (14 pages).
Khondker, O.A. et al., "Fabrication and mechanical properties of aramid/nylon plain knitted composites," Composites Part A: Applied Science and Manufacturing, 2004. 35(10): p. 1195-1205 (11 pages).
Kim, Nam K. et al., "Nanofibrillar Poly(vinylidene fluoride): Preparation and Functional Properties," Int. J. Polym. Mater. Polym. Biomater., 2014. 63(1): p. 23-32 (10 pages).
Kim, Nam K. et al., "Polymer-Polymer and Single Polymer Composites Involving Nanofibrillar Poly(vinylidene Fluoride): Manufacturing and Mechanical Properties," J. Macromol. Sci., Part B: Phys., 2014. 53(7): p. 1168-1181 (14 pages).
"Liquid-Crystal Polymer," Wikipedia, the Free Encyclopedia <http://en/wikipedia.org/wiki/Liquid-crystal_polymer>, retrieved Jun. 2, 2016 (3 pages).
Liu, et al., "Effect of fiber orientation on the stress distribution within a leaflet of a polymer composite heart valve in the closed position," J of Biomedichanics, 2007, 40:1099-1106 (8 pages).
Maity, J. et al., "Homocomposites of chopped fluorinated polyethylene fiber with low-density polyethylene matrix," Mater. Sci. Eng., A, 2008. A479(1-2): p. 125-135 (11 pages).
Matabola, K. P. et al., "Single polymer composites: a review," Journal of Materials Science, 2009. 44(23): p. 6213-6222 (10 pages).
Medeiros Araujo, Thiago et al., "Liquid crystalline single-polymer short-fibers composites," Composite Interfaces, 2013. 20(4): p. 287-298 (12 pages).
Ohri, Rachit et al., "Hyaluronic acid grafting mitigates calcification of glutaraldehyde-fixed bovine pericardium," J Biomed Mater Res 70A: 328-334, 2004 (7 pages).
Schneider, Tobias et al., "Influence of fiber orientation in electrospun polymer scaffolds on viability, adhesion and differentiation of articular chondrocytes," Clinical Hemorheology and Microcirculation 52 (2012) 325-336 (13 pages).
Sun, Xiaoli et al., "α and β Interfacial Structures of the iPP/PET Matrix/Fiber Systems," Macromolecules, 2007. 40(23): p. 8244-8249 (6 pages).
Vick, Linda W. et al., "Hot compaction and consolidation of polycarbonate powder," Polym. Eng. Sci., 1998. 38(11): p. 1824-1837 (14 pages).
Wang, Qiang et al., "A novel small animal model for biocompatibility assessment of polymeric materials for use in prosthetic heart valves," J Biomed Mater Res 93A: 442-453, 2010 (12 pages).
Wang, Qiang et al., "In-Vivo Assessment of a Novel Polymer (SIBS) Trileaflet Heart Valve," J Heart Valve Dis, Jul. 2010, 19(4):499-505 (7 pages).
Ward, I.M. et al., "Developments in oriented polymers," Plastics, Rubber and Composites, 2004. 33(5): p. 189-194 (6 pages).
Ward, I.M. et al., "Novel composites by hot compaction of fibers," Polym. Eng. Sci., 1997. 37(11): p. 1809-1814 (6 pages).
Wheatley, et al., "Polyurethane: material for the next generation of heart valve prostheses?," Eur J Cardio-Thoracic Surg, 2000, 17:440-448 (11 pages).
Yang, Mingjing et al., "Assessing the Resistance to Calcification of Polyurethane Membranes Used in the Manufacture of Ventricles for a Totally Implantable Artificial Heart," J Biomed Mater Res (Appl Biomater) 48: 648-659, 1999 (12 pages).
Yao, Jian et al., "High Strength and High Modulus Electrospun Nanofibers," Fibers 2014; 2:158-187 (30 pages).
Yeh, Shiou-Bang et al., "Modification of Silicone Elastomer with Zwitterionic Silane for Durable Antifouling Properties," Langmuir 2014, 30, 11386-11393 (8 pages).
Zhang, Baoyan et al., "Studies of Novel Segmented Copolyether Polyurethanes," Eur. Polym. J., vol. 34, No. 3-4, pp. 571-575 (1998) (5 pages).
Zhang, Zhiping et al., "Effect of Crosslinking and Grafting by 60Co-γ-ray Irradiation on Carbon Black/Polyethylene Switching Materials and Fluoride Resin System in self-regulating Heating Cables," JAERI-Conf, 2000. 2000-001(JCBSRC '99, the 8th Japan-China Bilateral Symposium on Radiation Chemistry, 1999): p. 202-210 (9 pages).
Zhao, Zeng Hua et al., "Research development of single polymer composite preparation," Gongcheng Suliao Yingyong, 2010. 38(2): p. 81-84, with machine translation (11 pages).

(56) References Cited

OTHER PUBLICATIONS

"International Search Report and Written Opinion," for PCT Application No. PCT/US2016/041757 dated Oct. 12, 2016 (12 pages).
"International Search Report and Written Opinion," for PCT application No. PCT/US2016/050691 dated Dec. 19, 2016 (14 pages).
Kuang, Jinghao et al., "Universal Surface-initiated Polymerization of Antifouling Zwitterionic Brushes Using a Mussel Mimetic Peptide Initiator," Langmuir. May 8, 2012; 28(18): 7258-7266 (20 pages).
"Response to Communication Pursuant to Article 94(3) EPC," for European Patent Application No. 13739321.1 filed with the EPO dated Jan. 2, 2017 (37 pages).
"Response to Final Office Action," for U.S. Appl. No. 14/656,044, dated Sep. 9, 2016 and filed with the USPTO Dec. 8, 2016 (9 pages).
"Second Office Action," for Chinese Patent Application No. 201380044842.0, dated Aug. 12, 2016 (16 pages) with summary.
Tu, Qin et al., "Synthesis of Polyethylene Glycol- and Sulfobetaine-Conjugated Zwitterionic Poly(l-lactide) and Assay of its Antifouling Properties," Colloids and Surfaces B; Biointerfaces 102 (2013) 331-340 (10 pages).
Cacciola, G. et al., "A Synthetic Fiber-Reinforced Stentless Heart Valve," Journal of Biomechanics, Jan. 1, 2000, pp. 653-658, XP055284947, Retrieved from the Internet: URL:http://ac.els-cdn.com.
Cacciola, G. et al., "A Three-Dimensional Mechanical Analysis of a Stentless Fibre-Reinforced Aortic Valve Prosthesis," Journal of Biomechanics, Jan. 1, 2000, pp. 521-530, XP055284955, Retrieved from the Internet: URL:http://ac.els-cdn.com.
"Communication Pursuant to Article 94(3) EPC," for European Patent Application No. 13739321.1 dated Sep. 8, 2016 (4 pages).
"Final Office Action," for U.S. Appl. No. 14/656,044 dated Sep. 9, 2016 (17 pages).
Gallocher, "Durability Assessment of Polymer Trileaflet Heart Valves," (2007). FIU Electronic Theses and Dissertations, Paper 54 (237 pages).
"International Search Report and Written Opinion," for PCT/US2016/024614 dated Jul. 12, 2016 (13 pages).
"International Search Report and Written Opinion," for PCT/US2016/024753 dated Jul. 22, 2016 (11 pages).
"International Search Report and Written Opinion," for PCT/US2016/039808 dated Sep. 26, 2016 (11 pages).
Kalejs, et al., "St. Jude Epic Heart Valve Bioprostheses Versus Native Human and Porcine Aortic Valves—Comparison of Mechanical Properties," Interactive Cardiovascular and Thoracic Surgery 8 (2009) 553-557.
Masoumi, et al., "Trilayered Elastomeric Scaffolds for Engineering Heart Valve Leaflets," Biomaterials. Sep. 2014; 35(27):7774-7785.
"Response to Non-Final Office Action," for U.S. Appl. No. 14/656,044, dated May 20, 2016 and filed with the USPTO Aug. 9, 2016 (11 pages).
Vesely, et al., "Micromechanics of the Fibrosa and the Ventricularis in Aortic Valve Leaflets," J Biomech. 1992 25(1):101-113.
Berkland, Cory et al., "Controlling surface nano-structure using flow-limited field-injection electrostatic spraying (FFESS) of poly(D,L-lactide-co-glycolide)," Biomaterials (2004) 25: 5649-5658.
Fabreguette, et al., "X-ray mirrors on flexible polymer substrates fabricated by atomic layer deposition," Thin Solid Films 515: 7177-7180 (2007).
Fabreguette, Francois H. et al., "Ultrahigh x-ray reflectivity from W/Al2O3 multilayers fabricated using atomic layer deposition," Applied Physics Letters 88: 013166 (2006), 3 pages.
"Final Office Action," for U.S. Appl. No. 15/193,794 dated May 23, 2018 (12 pages).
George, "Final Report—Fabrication of Nanolaminates with Ultrathin Nanolayers Using Atomic Layer Deposition: Nucleation & Growth Issues," AFOSR Grant No. FA9550-01-1-0075 Feb. 2009 (36 pages).
Groner, M. D. et al., "Gas Diffusion Barriers on Polymers Using Al2O3 Atomic Layer Deposition," Applied Physics Letters 88, 051907, 2006 (3 pages).

Hass, D. D. et al., "Reactive vapor deposition of metal oxide coatings," Surface and Coatings Technology 146-147 (2001) 85-93.
"International Preliminary Report on Patentability," for PCT Application No. PCT/US2016/024614 dated Oct. 19, 2017 (7 pages).
"International Preliminary Report on Patentability," for PCT Application No. PCT/US2016/024753 dated Oct. 19, 2017 (7 pages).
"International Preliminary Report on Patentability," for PCT Application No. PCT/US2016/039808 dated Jan. 11, 2018 (8 pages).
"International Preliminary Report on Patentability," for PCT Application No. PCT/US2016/041757 dated Jan. 25, 2018 (8 pages).
"International Preliminary Report on Patentability," for PCT Application No. PCT/US2016/050691 dated Mar. 29, 2018 (9 pages).
"International Search Report and Written Opinion," for PCT Application No. PCT/US2017/032656 dated Jul. 21, 2017 (16 pages).
Jen, Shih-Hui et al., "Critical tensile and compressive strains for cracking of al2O3 films grown by atomic layer deposition," Journal of Applied Physics 109, 084305 (2011), 11 pages.
Jen, Shih-Hui et al., "Critical tensile strain and water vapor transmission rate for nanolaminate films grown using al2o3 atomic layer deposition and alucone molecular layer deposition," Applied Physics Letters 101, 234103 (2012), 3 pages.
Mach, H. et al., "Highly Reactive Polyisobutene as a Component of a New Generation of Lubricant and Fuel Additives," Lubrication Science 1999, 11 (2), 175-185.
"Non-Final Office Action," for U.S. Appl. No. 15/193,794 dated Mar. 14, 2018 (14 pages).
"Non-Final Office Action," for U.S. Appl. No. 15/193,794 dated Nov. 6, 2017 (32 pages).
"Non-Final Office Action," for U.S. Appl. No. 15/257,211 dated Apr. 10, 2018 (39 pages).
"Notification of Patent Reexamination," for Chinese Patent Application No. 201380044842.0 dated Feb. 7, 2018 (12 pages) with English summary.
Raghavan, R. et al., "Nanocrystalline-to-amorphous transition in nanolaminates grown by low temperature atomic layer deposition and related mechanical properties," Applied Physics Letters 100, 191912 (2012), 9 pages.
"Response to Communication Pursuant to Rules 161(1) and 162 EPC," for European Patent Application No. 16715218.0 filed May 25, 2018, 13 pages.
"Response to Communication Pursuant to Rules 161(1) and 162 EPC," for European Patent Application No. 16715724.7 filed May 25, 2018, (7 pages).
"Response to Non-Final Office Action," for U.S. Appl. No. 15/193,794, dated Mar. 14, 2018 and filed with the USPTO Apr. 16, 2018 (8 pages).
"Response to Non-Final Office Action," for U.S. Appl. No. 15/193,794, dated Nov. 6, 2017 and filed with the USPTO Feb. 13, 2018 (7 pages).
"Response to Non-Final Office Action," for U.S. Appl. No. 15/257,211, dated Apr. 10, 2018 and filed with the USPTO Jun. 18, 2018 (10 pages).
Rutledge, G.C. et al., "Electrostatic Spinning and Properties of Ultrafine Fibers," National Textile Center Annual Report: Nov. 2001, M01-D22, (10 pages).
Shin, Y. M. et al., "Experimental characterization of electrospinning: the electrically forced jet and instabilities," Polymer 42 (2001) 9955-9967.
Szeghalmi, Adriana et al., "All dielectric hard x-ray mirror by atomic layer deposition," Applied Physics Letters 94, 133111 (2009), 3 pages.
Szilagyi, Imre M. et al., "Review on One-Dimensional Nanostructures Prepared by Electrospinning and Atomic Layer Deposition," INERA Workshop of ISCMP2014, IOP Publishing, Journal of Physics: Conference Series 559, 2014 (13 pages).
Final Office Action for U.S. Appl. No. 15/257,211 dated Jul. 26, 2018 (13 pages).
Final Office Action for U.S. Appl. No. 15/797,394 dated Jan. 30, 2019 (12 pages).
First Office Action for Chinese Patent Application No. 20160036250.8 dated Nov. 2, 2018 (11 pages) with English Summary.
First Office Action for Chinese Patent Application No. 201680018700.0 dated Nov. 2, 2018 (12 pages) with English Summary.

(56) References Cited

OTHER PUBLICATIONS

International Preliminary Report on Patentability for PCT Application No. PCT/US2017/032656 dated Nov. 29, 2018 (7 pages).
International Search Report and Written Opinion for PCT Application No. PCT/US2018/028864 dated Jul. 30, 2018 (10 pages).
Madhusha, "Difference between Fluorine and Fluoride," Aug. 9, 2017, PEDIAA.com, pp. 1-8. URL <http://pediaa.com/difference-between-fluorine-and-fluoride/> (8 pages).
Non-Final Office Action for U.S. Appl. No. 15/082,293 dated Jul. 11, 2018 (41 pages).
Non-Final Office Action for U.S. Appl. No. 15/082,382 dated Sep. 19, 2018 (8 pages).
Non-Final Office Action for U.S. Appl. No. 15/193,794 dated Jan. 29, 2019 (25 pages).
Non-Final Office Action for U.S. Appl. No. 15/205,098 dated Oct. 30, 2018 (42 pages).
Non-Final Office Action for U.S. Appl. No. 15/595,176 dated Aug. 27, 2018 (30 pages).
Non-Final Office Action for U.S. Appl. No. 15/797,394 dated Sep. 26, 2018 (39 pages).
Notice of Allowance for U.S. Appl. No. 15/082,293 dated Jan. 17, 2019 (12 pages).
Notice of Allowance for U.S. Appl. No. 15/082,382 dated Jan. 25, 2019 (14 pages).
Notice of Allowance for U.S. Appl. No. 15/257,211 dated Sep. 24, 2018 (7 pages).
Response to Communication Pursuant to Rules 161(1) and 162 EPC, for European Patent Application No. 16736720.0 filed with the EPO Jul. 12, 2018 (12 pages).
Response to Communication Pursuant to Rules 161(1) and 162 EPC for European Patent Application No. 16766455.6 filed Dec. 4, 2018 (9 pages).
Response to Final Office Action for U.S. Appl. No. 15/193,794, dated May 23, 2018 and filed with the USPTO Jul. 17, 2018 (10 pages).
Response to Final Rejection dated Jul. 26, 2018, for U.S. Appl. No. 15/257,211, submitted via EFS-Web on Aug. 9, 2018, 5 pages.
Response to Non Final Office Action for U.S. Appl. No. 15/205,098, filed Dec. 27, 2018 (7 pages).
Response to Non-Final Rejection dated Aug. 27, 2018, for U.S. Appl. No. 15/595,176, submitted via EFS-Web on Nov. 26, 2018, 6 pages.
Response to Non-Final Rejection dated Jul. 11, 2018, for U.S. Appl. No. 15/028,293, submitted via EFS-Web on Oct. 11, 2018, 12 pages.
Response to Non-Final Rejection dated Sep. 19, 2018, for U.S. Appl. No. 15/082,382, submitted via EFS-Web on Dec. 18, 2018, 6 pages.
Response to Non-Final Rejection dated Sep. 26, 2018, for U.S. Appl. No. 15/797,394, submitted via EFS-Web on Dec. 19, 2018, 9 pages.
Notice of Allowance for U.S. Appl. No. 15/205,098 dated May 2, 2019 (16 pages).
Notice of Allowance for U.S. Appl. No. 15/959,176 dated Mar. 21, 2019 (13 pages).
Response to Communication Pursuant to Rules 161(1) and 162 EPC for European Patent Application No. 17725140.2 filed Apr. 2, 2019 (9 pages).
Response to Final Rejection dated Jan. 30, 2019, for U.S. Appl. No. 15/797,394, submitted via EFS-Web on Apr. 23, 2019, 8 pages.
Third Office Action for Chinese Patent Application No. 201380044842.0 dated Dec. 29, 2018 (12 pages), with English translation.

\* cited by examiner

FIBER REINFORCED PROSTHETIC HEART VALVE HAVING UNDULATING FIBERS

This application claims the benefit of U.S. Provisional Application No. 62/145,382 filed Apr. 9, 2015, the contents of which are herein incorporated by reference.

TECHNICAL FIELD

This invention relates to prosthetic heart valves having leaflets having undulating fibers embedded in a polymer matrix.

BACKGROUND

Heart function can be significantly impaired when a heart valve is not functioning properly. Potential causes for heart valve malfunction include dilation of an annulus around the valve, ventricular dilation, and a prolapsed or misshapen valve leaflet. When the heart valve is unable to close properly, blood within a heart chamber can leak backwards, commonly referred to as regurgitation, through the valve.

Valve regurgitation may be treated by replacing or repairing a diseased valve, such as an aortic valve. Surgical valve replacement is one method for treating the diseased valve, but other less invasive methods of treatments are also available to many patients. Minimally invasive methods of treatment, such as transcatheter aortic valve replacement (TAVR), generally involve the use of delivery devices that are delivered through arterial passageways or other anatomical routes into the heart to replace the diseased valve with an implantable prosthetic heart valve. There is a desire to reduce the profile of the devices used for delivery and implantation to minimize trauma to blood vessels during device delivery and implantation. Though in a crimped state during device delivery, the valve leaflet of a prosthetic heart valve can still significantly contribute to the device profile. Accordingly, there is a need to reduce to the valve leaflet thickness of prosthetic heart valves.

SUMMARY

Prosthetic heart valves provided herein can have a structure adapted to optimize functionality during the life of a patient and to provide anisotropic properties to synthetic leaflet materials. Prosthetic heart valves herein can include leaflets that include undulating fibers embedded in a polymer matrix.

In Example 1, a prosthetic heart valve including a composite material including a first plurality of fibers embedded in a polymer matrix. The prosthetic heart valve can be characterized by each fiber having a first extending direction and a plurality of undulations.

In Example 2, the prosthetic heart valve of Example 1, wherein composite material is included in a leaflet and at least a portion of the first plurality of fibers extends along at least a portion of an edge contour of a leaflet of the prosthetic heart valve.

In Example 3, the prosthetic heart valve of Example 1 or Example 2, wherein the first extending direction is one of a circumferential direction and a radial direction on a leaflet of the prosthetic heart valve.

In Example 4, the prosthetic heart valve of one of Examples 1-3, wherein the plurality of undulations of each fiber is adapted to straighten when the composite material is stretched in the first extending direction of the fibers.

In Example 5, the prosthetic heart valve of one of Examples 1-4, wherein the composite material is more elastic in a direction parallel to the first extending direction and less elastic in a direction oblique to the first extending direction.

In Example 6, the prosthetic heart valve of one of Examples 1-5, wherein the composite material has a first elasticity when an average segment distance of the plurality of fibers is less than an average total fiber length of the plurality of fibers and a second elasticity when the average segment distance of the plurality of fibers is equal to or greater than the average total fiber length of the plurality of fibers, wherein the first elasticity is greater than the second elasticity.

In Example 7, the prosthetic heart valve of one of Examples 1-6, wherein the undulations have a predetermined average amplitude ranging between 0.5 mm and 2 mm and a predetermined average wavelength ranging between 0.5 mm to 2 mm.

In Example 8, the prosthetic heart valve of one of Examples 1-7, wherein the plurality of fibers include a thermoplastic polymer.

In Example 9, the prosthetic heart valve of one of Examples 1-8, wherein the plurality of fibers include a liquid crystalline polymer.

In Example 10, the prosthetic heart valve of one of Examples 1-9, wherein the polymer matrix includes an elastomeric polymer.

In Example 11, the prosthetic heart valve of one of Examples 1-10, further including a second plurality of fibers embedded in the polymer matrix, each fiber having a second extending direction and a plurality of undulations.

In Example 12, the prosthetic heart valve of Example 11, wherein the direction of the first plurality of fibers defines a first longitudinal axis and the direction of the second plurality of fibers defines a second longitudinal axis, wherein the first longitudinal axis is orthogonal to the second longitudinal axis.

In Example 13, the prosthetic heart valve of Example 11, wherein the direction of the first plurality of fibers defines a first longitudinal axis and the direction of the second plurality of fibers defines a second longitudinal axis, wherein the first longitudinal axis is oblique to the second longitudinal axis.

In Example 14, a method of forming the prosthetic heart valve leaflet of Examples 1-12, that includes forming a composite material. The composite material is formed by disposing a first polymeric layer on a mandrel, disposing a plurality of fibers including a plurality of undulations onto the first polymeric layer, and disposing a second polymeric layer on the plurality of fibers.

In Example 15, the method of Example 14, wherein the plurality of fibers are disposed using an electro spinning process.

In Example 16, the prosthetic heart valve includes a composite material including a first plurality of fibers embedded in a polymer matrix. Each fiber has a first extending direction and a plurality of undulations, wherein the plurality of undulations of the first plurality of fibers are adapted to provide the composite material with multi-stage elastic properties.

In Example 17, the prosthetic heart valve of Example 16, wherein at least a portion of the first plurality of fibers extends along at least a portion of an edge contour of a leaflet of the prosthetic heart valve.

In Example 18, the prosthetic heart valve of Example 16, wherein the first extending direction is one of a circumferential direction and a radial direction on a leaflet of the prosthetic heart valve.

In Example 19, the prosthetic heart valve of Example 16, wherein the plurality of undulations of each fiber is adapted to straighten when the composite material is stretched in the first extending direction.

In Example 20, wherein the composite material is more elastic when the plurality of fibers have the plurality of undulations and less elastic when at least a portion of the plurality of fibers have been stretched into a substantially straight fibers.

In Example 21, wherein the composite material has a first elasticity when an average segment distance of the plurality of fibers is less than an average total fiber length of the plurality of fibers and a second elasticity when the average segment distance of the plurality of fibers is equal to or greater than the average total fiber length of the plurality of fibers, wherein the first elasticity is greater than the second elasticity.

In Example 22, the prosthetic heart valve of Example 16, wherein the undulations have a predetermined average amplitude and predetermined average wavelength.

In Example 23, the prosthetic heart valve of Example 16, wherein the plurality of fibers include a thermoplastic polymer.

In Example 24, the prosthetic heart valve of Example 16, wherein the plurality of fibers include a liquid crystalline polymer.

In Example 25, the prosthetic heart valve of Example 16, wherein the polymer matrix includes an elastomeric polymer.

In Example 26, the prosthetic heart valve of Example 16, further including a second plurality of fibers embedded in the polymer matrix, each fiber having a second extending direction and a plurality of undulations.

In Example 27, wherein the direction of the first plurality of fibers defines a first longitudinal axis and the direction of the second plurality of fibers defines a second longitudinal axis, wherein the first longitudinal axis is orthogonal to the second longitudinal axis.

In Example 28, wherein the direction of the first plurality of fibers defines a first longitudinal axis and the direction of the second plurality of fibers defines a second longitudinal axis, wherein the first longitudinal axis is oblique to the second longitudinal axis.

In Example 29, a prosthetic heart valve includes a tubular body having an annular region and a plurality of leaflets. Each leaflet has a free end and a bottom edge, which is coupled to the annular region of the tubular body. Each leaflet has a free edge substantially opposite the bottom edge. At least a portion of the leaflet made of a composite material includes a plurality of curved fibers embedded in a polymer matrix, wherein the plurality of curved fibers includes a liquid crystal polymer.

In Example 30, the prosthetic heart valve of Example 29, wherein the plurality of curved fibers are composed of a polyester-based liquid crystal polymer formed by the polycondensation of 4-hydroxybenzoic acid and 6-hydroxynaphthalene-2-carboxylic acid.

In Example 31, the prosthetic heart valve of Example 29, wherein the plurality of curved fibers are each encapsulated within a jacket including a polyurethane or a derivative of a polyurethane.

In Example 32, the prosthetic heart valve of Example 29, wherein each curved fiber of the plurality of curved fibers has a first extending direction and a plurality of undulations.

In Example 33, a method of forming a prosthetic heart valve leaflet that includes forming a composite material. The composite material is formed by disposing a first polymeric layer on a mandrel, disposing a plurality of fibers having a plurality of undulations on the first polymeric layer and disposing a second polymeric layer on the plurality of fibers, wherein the composite material is elastic when a plurality of fibers are in a relaxed state having a plurality of undulations and less elastic when at least a portion of the plurality of fibers are stretched into substantially straight fibers.

In Example 34, the method of Example 33, wherein the plurality of fibers are disposed using an electro spinning process.

In Example 35, the method of Example 33, wherein the first polymer layer is disposed on the mandrel using a dipping or spraying process.

The details of one or more embodiments of the devices, systems, and methods provided herein are set forth in the accompanying drawings and the description below. Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

Figure 1:
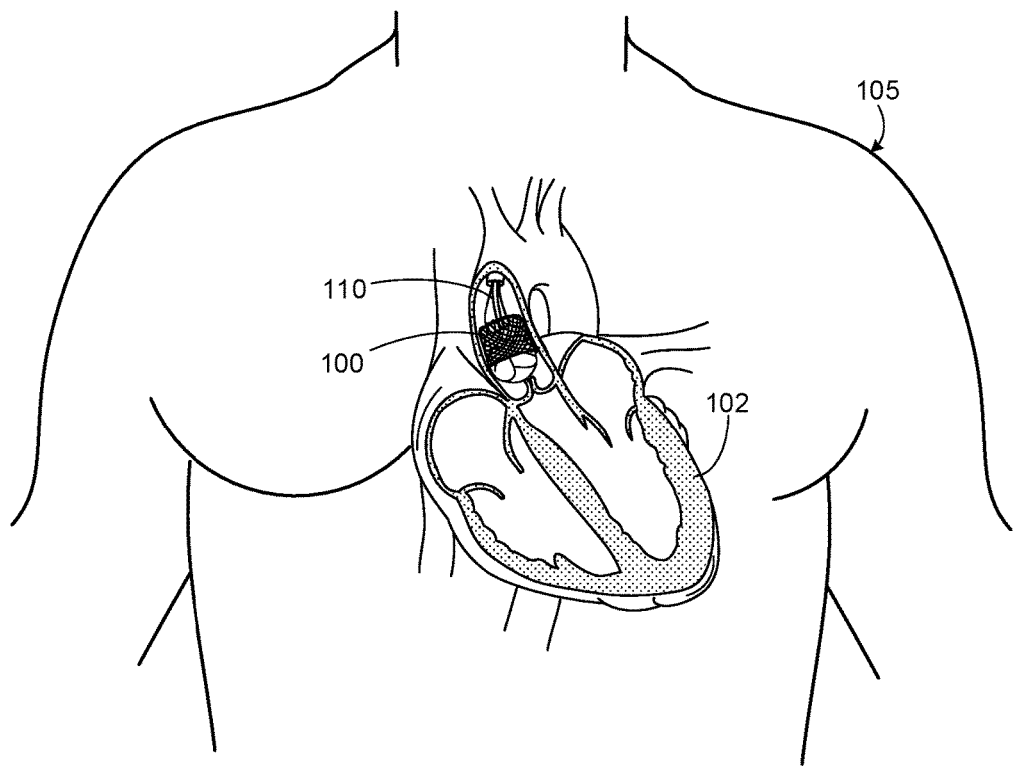
FIG. 1 is an illustration of an exemplary prosthetic heart valve within a human anatomy.
Figure 2:
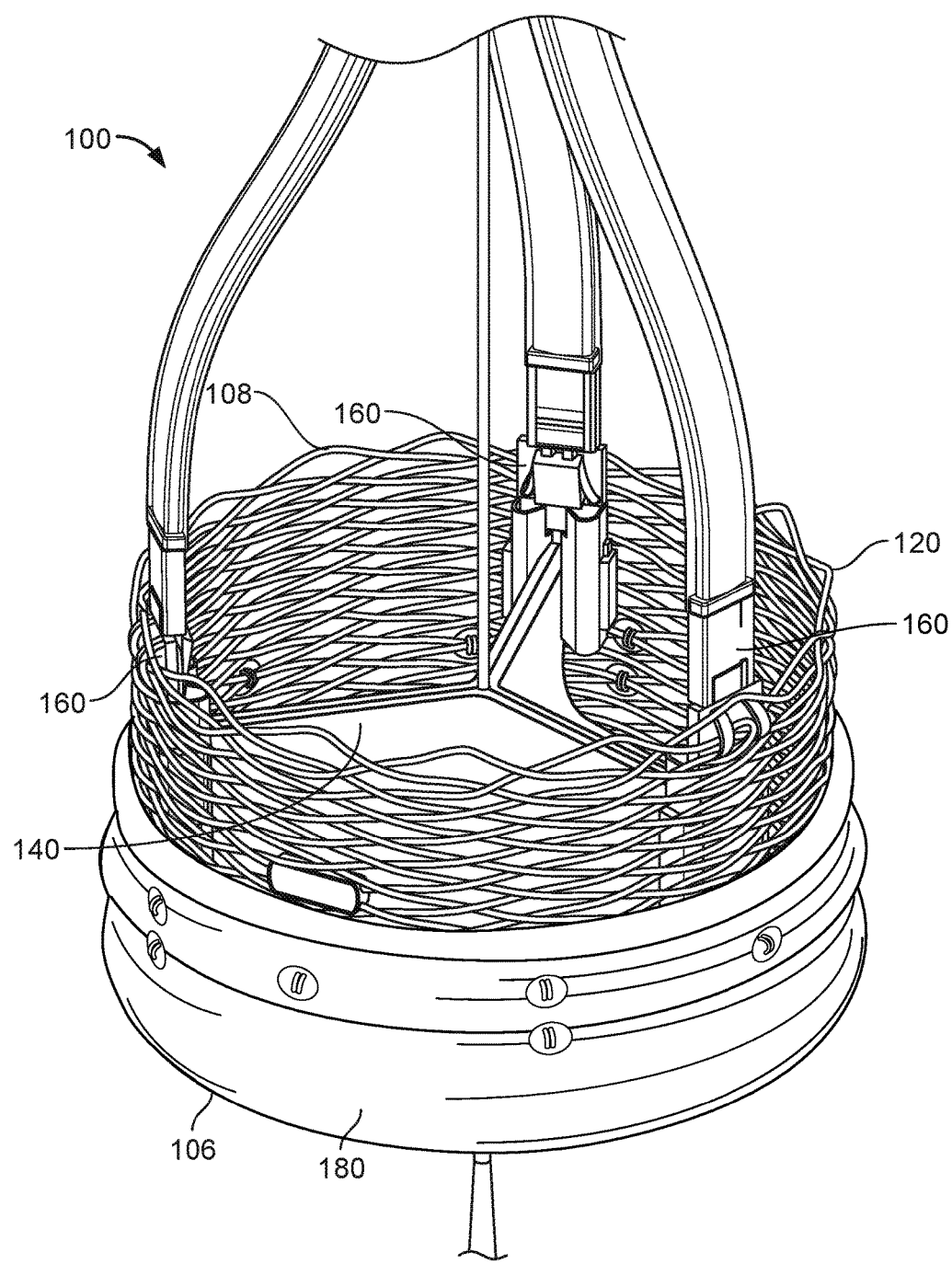
FIG. 2 is an enlarged view of the prosthetic heart valve of FIG. 1.

FIG. 1 shows an illustration of a prosthetic heart valve 100 provided herein within the heart 102 of a human body 105. The human body 105 has four heart valves: a pulmonary valve, a tricuspid valve, an aortic valve and a mitral valve. The purpose of the heart valves is to allow blood to flow through the heart and from the heart into the major blood vessels connected to the heart, such as the aorta and pulmonary artery. Prosthetic heart valve 100 of FIG. 1 is an aortic prosthetic heart valve that can be delivered using a transcatheter aortic valve replacement (TAVR) procedure (which is also described as percutaneous aortic valve replacement (PAVR) or transcatheter aortic valve implantation (TAVI)), which involves the use of a deployment device 110 (which can also be referred to as a delivery catheter or delivery system) placed through blood vessels from a femoral, subclavian, or direct aortic incision. Deployment device 110 can deliver prosthetic heart valve 100 to the desired location within the anatomy, and release implantable heart valve 100 at an implantation site. Although FIG. 1 shows an aortic prosthetic heart valve, it should be appreciated that prosthetic heart valve 100 can be another type of heart valve (e.g., a mitral valve or a tricuspid valve), in some cases. In some cases, the prosthetic heart valve provided herein can be generally applicable to valves within the body, FIG. 2 provides a close up view of the prosthetic heart valve 100 of FIG. 1 having inflow end 106 and an outlet end 108. Prosthetic heart valve 100 has a substantially tubular body 120, a plurality of leaflets 140, anchor elements 160 and a tubular seal 180. Tubular body 120 can be a radially expandable member, e.g. annular frame or stent, having an annular cavity. As shown in FIG. 2, the heart valve 100 can have three heart valve leaflets 140 coupled to the tubular body 120 within the annular cavity. Three anchor elements 160 positioned within the annular cavity of the tubular body 120 can each secure the heart valve leaflets to the tubular body 120. Each anchor elements 160 can be coupled to the tubular body 120 with an anchoring element and coupled to the leaflets with a clamping element. The tubular seal 180 can be disposed about at least a portion of the tubular body 120. In particular, the tubular seal can have an inflow end portion (not shown) secured to bottom edges of the plurality of leaflets and have an outflow end portion 108 disposed about an outer surface of the tubular body 120 to restrict blood flow around the leaflets.

Prosthetic heart valve 100 can be made of various materials. In some cases, at least a portion of the prosthetic heart valve 100, for example, the leaflets 140 or a portion of the tubular body 120, can be made of various synthetic materials. In some cases, the prosthetic heart valve 100 can be entirely made of synthetic materials. The synthetic materials of the prosthetic heart valve 100 can include polymeric materials, metals, ceramics, and combinations thereof. In some cases, synthetic materials of the prosthetic heart valve 100 can include a composite material composed of at least two constituent materials with different physical and/or chemical properties. By incorporating different materials with different properties into a leaflet composite material, the physical, chemical and/or mechanical properties of the composite material can be tailored, as desired.

In use, prosthetic heart valve 100 is implanted (e.g., surgically or through transcatheter delivery) in a mammalian heart. The edge portions of the polymeric leaflets 140 move into coaptation with one another in a closed position to substantially restrict fluid from flowing past prosthetic heart valve 100 in a closed position. The edge portions of the leaflets 140 move away from one another to an open position permitting fluid to flow past prosthetic heart valve 100. Movement of the leaflets between the closed and open positions can substantially approximate the hemodynamic performance of a healthy natural valve.

In some cases, the leaflet 140 can be partially made from tissue obtained from an animal, e.g., a pig or a cow. In some cases, for example, a portion of the leaflet 140 can be made from bovine pericardium or porcine tissue.

Figures 3A, 3B:
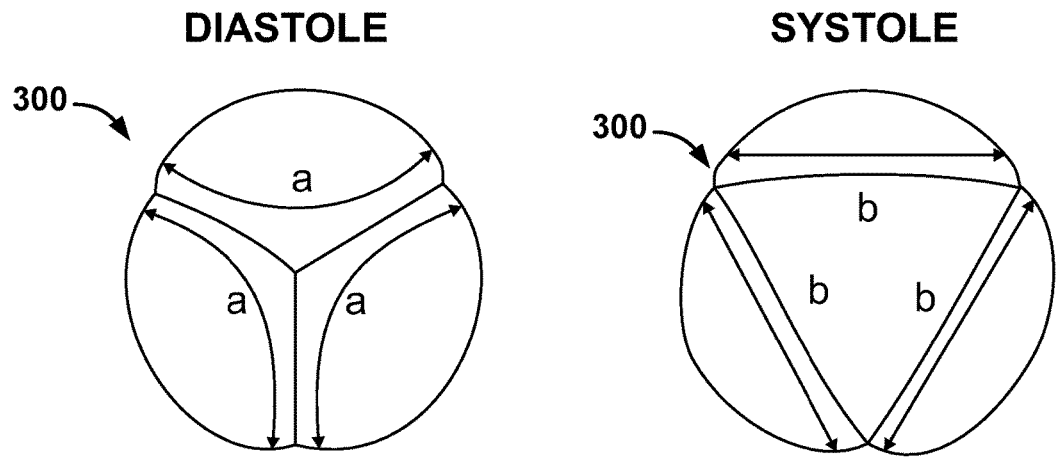
FIGS. 3A and 3B are illustrations of a prosthetic heart valve provided herein that show strain curves at diastole and systole, respectively.

FIGS. 3A and 3B show leaflets 300 of an exemplary prosthetic heart valve discussed herein during various time periods of a cardiac cycle. In particular, FIG. 3A shows prosthetic heart valve during diastole and FIG. 3B shows prosthetic heart valve during systole. Diastole is the time period of a cardiac cycle at which a heart chamber fills with blood and the surrounding heart muscles are relaxed. Ventricular diastole is the period at which the ventricles are filling with blood and the ventricular walls are in a relaxed state, while atrial diastole is the period at which the atriums are filling with blood and the atrial walls are relaxed. Systole is the time period of a cardiac cycle at which blood in the heart chamber empties and the heart chamber muscles are in a contracted state due to a response to an electrochemical stimulus.

Leaflets 300 are strained in different locations and with different intensities during various periods of the cardiac cycle. As shown in FIG. 3A, three polymeric leaflets 300 of a prosthetic heart valve are at a closed state during diastole. The three leaflets 300 form a commissure when the valve is in a close state. As shown, the strain curves "a" of the leaflets 300 extend in an arc-shaped profile near a commissure.

Referring to FIG. 3B, prosthetic heart valve is shown with three polymeric leaflets 300 at an open state during systole. The open end of the leaflets 300 separate as blood is allowed to pass through the valve. Unlike the strain curves a shown in FIG. 3A, strain curves "b" of the leaflets during systole can extend along a chord length defined by the two points where each leaflet 300 connects to an adjacent leaflet and the tubular body.

Figure 4:
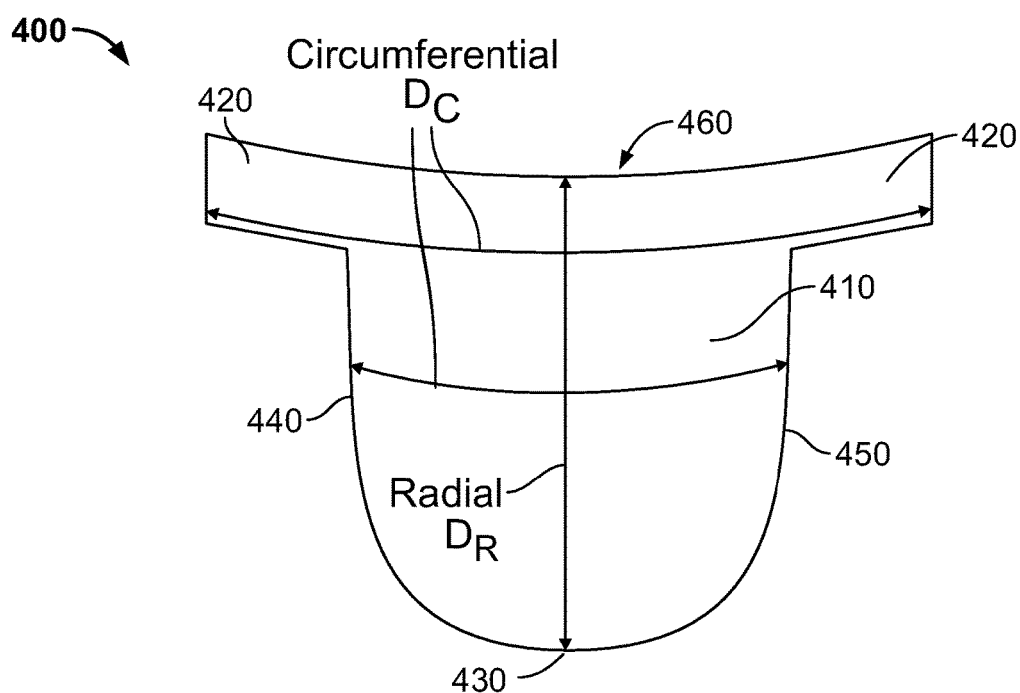
FIG. 4 provides an illustration of an exemplary leaflet provided herein.

FIG. 4 shows an example of a prosthetic heart valve leaflet 400 provided herein. As shown, leaflet 400 can include a body portion 410 (or belly region of the leaflet) and two sleeve portions 420 that extend outwardly from the body portion 410. In some cases, the body portion 410 has a bottom edge 430, a first side edge 440, a second side edge 450, and a free edge 460. Leaflet 400 further includes a front side (i.e., the side that blood flows toward), a back side (i.e., the side that blood flows away from). The bottom and side edges 410, 430 of the body portion 410 can be shaped for suturing and for forming a leaflet profile similar to a native valve. The sleeve portions 420 can be shaped to be compatible with anchor elements, such as anchor elements 160 of FIG. 2.

As the prosthetic heart valve opens and closes, each leaflet flexes between an open and a closed position. Tensile and flexural strain on each leaflet can change depending on its position. As such, the leaflet 400 can elongate in various directions as the valve opens and closes. For instance, leaflet 400 can elongate in a radial direction $D_R$ and a circumferential direction $D_C$ along the body portion 410 and/or the sleeve portions 420. The radial direction $D_R$ of a leaflet in a heart valve can extend radially inwardly or outwardly, e.g., a radial direction can extend from the center of the heart valve along a commissure line to a tubular body. The circumferential direction $D_C$ can extend along a circumference of a heart valve, e.g., an inner circumference of the tubular body 120 of FIG. 2. As shown in FIG. 4, the radial direction $D_R$ extends from the free edge 460 to the bottom edge 430 of the leaflet. A circumferential direction $D_C$ extends in a direction that is generally orthogonal to the radial direction $D_R$. More specifically, the circumferential direction $D_C$ extends from one side edge to the opposite side edge of the sleeve portion. The circumferential direction $D_C$ can also extend from one side of the body portion (e.g., the first side edge 440) to an opposite side of the body portion (e.g., the second side edge 450), which can be described as a circumferential direction $D_c$ in the belly region of the leaflet 400. In some cases, the leaflet 400 can elongate in a direction having an angle that is oblique relative to the radial and circumferential directions.

Figure 5:
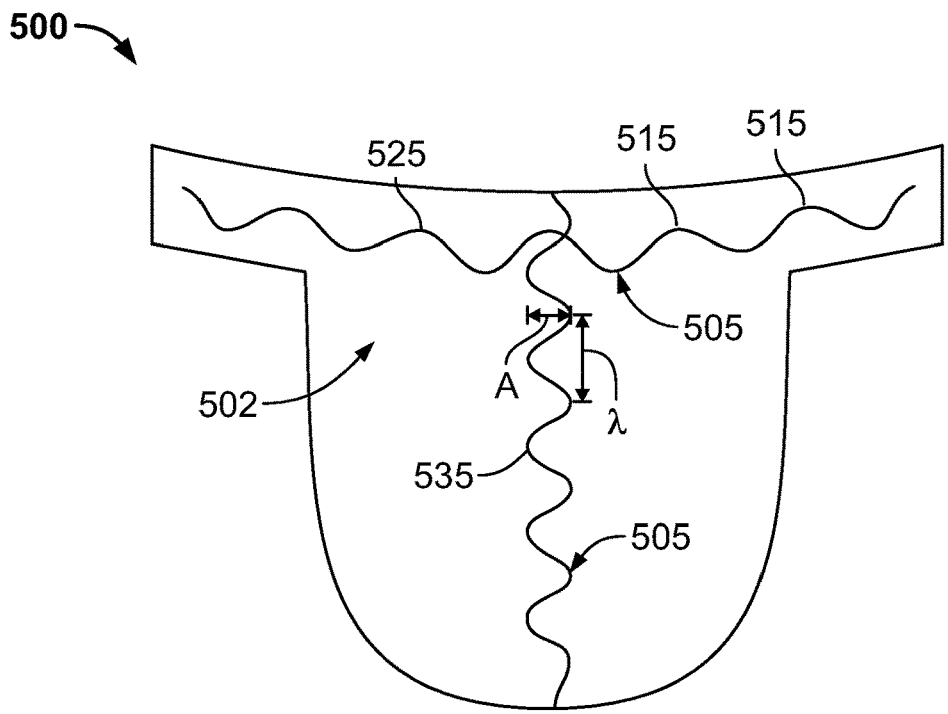
FIGS. 5 and 6 show various fiber configurations of a composite material for an exemplary leaflet provided herein.

FIG. 5 shows an exemplary prosthetic heart tissue valve leaflet 500 having a composite material that includes a plurality of fibers 505 embedded in a polymer matrix 502. As shown in FIG. 5, each fiber 505 has an extending direction (which can also be described as an orientation) and includes a plurality of undulations 515. In some cases, each undulation defines a crest that is orthogonal or oblique to the extending direction. In some cases, a fiber shape 505 of the fibers 505 provided herein can be described as a repeating wave or curve pattern within the polymer matrix 502. In some cases, the fibers 505 can be described as having a sinusoidal configuration and/or a plurality of orientations. The plurality of undulations and other non-linear configurations provide the composite material with multi-stage elasticity properties discussed herein.

Each fiber 505 can have a plurality of undulations, in which each undulation 515 has an amplitude "A" and a wavelength "λ." The plurality of undulations of each fiber 505 thus has an average amplitude and an average wavelength. In some cases, the amplitude or the average amplitude of a plurality of undulations can range from 0.1 mm (or 100 microns) to 5 mm. In some cases, the amplitude or the average amplitude of a plurality of undulations can range from 0.5 mm to 2 mm. In some cases, the wavelength or the average wavelength of a plurality of undulations can range from 0.1 mm to 3 mm. In some cases, the wavelength or the average wavelength of a plurality of undulations can range from 0.2 mm to 2 mm. Each fiber 505 can be defined by a total fiber length and a segment distance. The total fiber length is the length of the fiber if its undulations were straightened out and the fiber was straight when measured. The segment distance is the distance between where the fiber 505 starts to the where the fiber ends. Elasticity properties of the composite material can be adjusted, as desired, by modifying the amplitude and wavelength of the undulations.

Fibers 505 having a plurality of undulations can provide a benefit of producing a composite material with multi-stage elastic properties. The composite material has multistage elastic properties when the elasticity characteristics are influenced by two or more materials. For example, the composite material can exhibit an initial elastic characteristic and a subsequent elastic characteristic. The bending stiffness of the undulations in the fibers and the material properties of the polymer matrix 502 contribute to the initial elastic characteristic of the composite material when first stretched. As the composite material continues to be stretched, the polymer matrix 502 that surrounds each fiber 505 stretches and the undulations of individual fiber can become straightened. Eventually after one or more fibers 505 become straight, the composite material exhibits the subsequent elastic characteristic because the fibers 505 begin to significantly reduce the elasticity and increase the tensile strength of the composite material. The composite material is therefore more elastic when the plurality of fibers 505 include a plurality of undulations and less elastic when at least some of the plurality of fibers 505 have become stretched into a substantially straight fibers. The composite material can exhibit an elasticity similar to the polymer matrix when the plurality of fibers 505 include a plurality of undulations and an elasticity similar to the fiber material once the fibers 505 have become straight. In some cases, the elasticity of the composite material can become significantly reduced when the total fiber length of at least a portion of its fibers 505 is about equal to or greater than the segment distance, i.e., the distance between where the fiber starts and ends. In some cases, for example, the composite material can have a first elasticity when an average fiber length is less than an average fiber segment distance and a second elasticity when the average fiber length is about equal to or greater than the average fiber segment distance.

Still referring to FIG. 5, at least a portion of the plurality of fibers 502 can extend in a circumferential direction provided herein and at least a portion of the plurality of fibers 505 can extend in a radial direction provided herein on leaflet 500. As shown, circumferentially-directed fibers 525 can extend from one side edge to the opposite side edge of a sleeve portion and radially-directed fibers 535 can extend from a free edge to a bottom edge of the leaflet 500. In some cases, a majority or generally all of the fibers 505 extend in the circumferential direction or the radial direction. In some cases, the ratio of fibers 505 extending in the circumferential direction to the radial direction can be about 1:1. In some cases, the ratio of fibers 505 that extend from the circumferential direction to the radial direction can range from 1:10 to 1:5, from 1:5 to 1:4, from 1:4 to 1:3, form 1:3 to 1:2, from 1:2 to 1:1, from 1:1 to 2:1, from 2:1 to 3:1, from 3:1 to 4:1, from 4:1 to 5:1, from 5:1 to 10:1, from 1:10 to 10:1, from 1:5 to 5:1, from 1:4 to 4:1, from 1:3 to 3:1, from 1:2 to 2:1, from 1:10 to 5:1, from 1:10 to 4:1, 1:10 to 3:1, from 1:10 to 2:1, from 1:10 to 1:1, from 1:1 to 1:10, from 1:2 to 1:10, from 1:3 to 1:10, from 1:4 to 1:10, from 1:5 to 1:10, from 1:6 to 1:10, from 1:7 to 1:10, from 1:8 to 1:10, or from 1:9 to 1:10. The ratio of fibers 505 extending in the circumferential direction to the radial direction can provide the composite material with anisotropic or isotropic properties, as desired.

The composite material of leaflet 500 can include a polymer matrix 502 with multiple pluralities of fibers 505. In some embodiments, composite materials can include a first plurality of fibers 505 and a second plurality of fibers 505 both embedded in the polymer matrix 502, for example. Fibers 505 of the first plurality of fibers can have a first extending direction and a plurality of undulations. Fibers 505 of a second plurality of fibers can have a second extending direction and a plurality of undulations. In some cases, the plurality of undulations can be described as transversal waves that have crests that are orthogonal or oblique to the first extending direction. In various cases, the first extending direction can be different from the second extending direction. In some cases, the first and second directions can define first and second longitudinal axes, respectively. In some cases, the first longitudinal axis is orthogonal to the second longitudinal axis. In some cases, the first longitudinal axis is oblique to the second longitudinal axis. The extending direction(s) of fibers of a composite material can provide isotropic properties because the composite material will be more elastic in a direction parallel to the extending direction and less elastic in a direction orthogonal or oblique to the extending direction.

Fibers 505 of the leaflets 500 provided herein can be made of various materials. In various cases, fibers 505 can be made of a medically suitable fiber material. Suitable fiber materials that use polymers can include, but are not limited to, polypropylenes, polyesters, polytetrafluoroethylenes (PTFE) such as TEFLON® by E.I. DuPont de Nemours & Co., polyethylenes, polyurethanes, polyamides, nylons, polyetheretherketones (PEEK), polysulfones, fiberglass, acrylics, tantalum, polyvinyl alcohols, carbon, ceramics, metals (e.g., titanium, stainless steel), and combinations thereof. In some cases, suitable polymers for forming fibers 505 made from polyurethanes, for example, polyurethane elastomers (e.g. Pellethane), polyether-based polyurethanes (e.g. Tecothane), polycarbonate-based polyurethanes (e.g. Bionate and/or Chronoflex) and combinations thereof. Some examples of suitable polymer materials for fibers 505 include, but are not limited to, polycarbonate, polyether, polyester, polyamide, nylon 6, nylon 12, polyetherimide and combinations thereof. In some cases, fibers 505 can be made of a silk-based biomaterial. Silk-based biomaterials can include materials constructed from silk proteins such as silkworm fibroin, spider fibroin or *Bombyx mori* silk fibroin. In some cases, fibers 505 can be composed of silk-like materials such as fibronectin, elastin, or other silk-like proteins, for example, aneroin which is a protein derived from the sea anemone *Nematostella vectensis*.

In some cases, fibers 505 within the composite material of a leaflet 500 provided herein can be made of a liquid crystalline polymer (LCP). LCPs are a special class of aromatic polyester and/or polyamide copolymers that have semi-crystalline properties due to regions of highly ordered crystalline structures formed therein. Suitable fiber materials made of LCPs include, but are not limited to, thermotropic polyester such as Vectran®, poly(p-phenylene terephthalamide) (PPTA), and poly(phenylene benzobisoxazole) (PBO) and combinations thereof. Well-known LCPs include Kevlar®, Vectran®, Nomex®, Herachron®, Technora®, Twaron®, and Zylon®. In some cases, high performance fibers can be utilized in composite materials, such as gel-spun ultra-high molecular weight polyethylene (Dyneema®).

LCPs are generally chemically inert and have a high creep resistance, a high modulus and a high tensile strength. LCPs provide the advantage of using materials with thinner and smaller dimensions, e.g., composite layer thickness or fiber diameter, without compromising strength, robustness and durability. In some cases, the diameter of LCP fibers can be as small as 0.5 micrometers (microns), or about 0.00002 inches, and a total thickness of a leaflet 500 provided herein composed of LCP fibers can be as thin as about 50 microns to about 100 microns (or about 0.002 to about 0.004 inches).

In some cases, individual fibers 505 of a composite material can be encapsulated within a jacket (e.g., a polymer jacket) to promote bonding between the fibers 505 and the polymer matrix 502. In some cases, for example, the leaflet 500 provided herein can include LCP fibers that have been encapsulated within a polymer jacket. Suitable materials for the polymer jacket include, but are not limited to, polyurethane and derivatives of polyurethane. In some cases, the polymer jacket can be made of a polyisobutylene polyurethane copolymer.

Leaflets 500 provided herein can include composite materials having fiber diameters that can range from about 0.5 microns to about 200 microns (or about 0.00002 inches to about 0.0079 inches). In some cases, fibers 505 can have diameters or average diameters of at least 1 micron (or 0.00004 inches). Fibers can be, in some cases, in the range of about 1 micron to about 100 microns (or about 0.00004 inches to about 0.004 inches), including all ranges and values therebetween. In some cases, for example, suitable fiber diameter sizes can include ranges of about 1 micron to 5 microns (or about 0.00004 inches to about 0.0002 inches), 5 microns to 10 microns (or 0.0002 inches to about 0.0004 inches), 10 microns to 20 microns (or 0.0004 inches to about 0.0008 inches), 20 microns to 50 microns (or 0.0008 inches to about 0.0020 inches), and 50 microns to 100 microns (or 0.002 inches to about 0.004 inches). In some cases, fibers 505 can have diameters in the range of about 1 microns to about 10 microns (or 0.0004 inches to about 0.0020 inches), including all ranges and values therebetween. In some cases, the fiber made from polymers can range from about 5 microns to about 100 microns (or 0.00002 inches to about 0.0040 inches), from about 10 microns to about 75 microns (or 0.0004 inches to about 0.003 inches), from about 10 micron to about 50 microns (or 0.0004 inches to about 0.0020 inches), from about 20 microns to about 100 microns (or 0.0008 inches to about 0.0040 inches), from about 25 microns to about 200 microns (or 0.001 inches to about 0.008 inches), or from about 20 microns to about 50 microns (or 0.0008 inches to about 0.002 inches). In some cases, fibers 505, such as LCP fibers, can range from 0.5 microns (or 500 nanometers) to 5 microns (or about 0.00002 inches to about 0.00020 inches).

The polymer matrix 502 can be made of various polymeric materials. In some cases, the polymer matrix 502 can be made of an elastomeric polymer. Suitable polymer matrix materials include, but are not limited to, homopolymers, copolymers and terpolymers. Various polyurethanes can be used to construct the polymer matrix 502, such as polyurethanes with soft segments such as polyether, perfluoropolyether, polycarbonate, polyisobutylene, polysiloxane, or combinations thereof. Polyurethane hard segments can include, but are not limited to, methylene diphenyl diisocyanate (MDI), 4,4'-Methylene dicyclohexyl diisocyanate (H12MDI) and hexamethylene (HMDI). In some embodiments, the polymer matrix 502 can be formed from block polymers such as, for example, poly(styrene-isobutylene-styrene) (SIBS) tri-block polymers. Some suitable elastomeric materials include, but are not limited to, silicones, nitrile rubber, fluoroelastomers, polyolefin elastomers, latex-type elastomers, various natural elastomers such as those made from collagen, elastin, cellulose, proteins, carbohydrates and combinations thereof.

In some cases, for example, a leaflet 500 provided herein includes a composite material having a polymer matrix 502 composed of polyurethanes provided herein and a plurality of fibers composed of Vectran®, which is presently manufactured by Kuraray Co., Ltd. Vectran® is a polyester-based LCD made by the polycondensation of 4-hydroxybenzoic acid and 6-hydroxynaphthalene-2-carboxylic acid.

In some cases, an outer surface of a composite material can include zwitterionic polymers to reduce the calcification propensity of one or more synthetic materials. In some cases, a zwitterionic polymer includes a backbone with a zwitterionic group (which can also be described as a zwitterionic species or a zwitterionic compound). A zwitterionic group, or a zwitterion (also described as a dipolar ion or an inner salt), is a neutrally charged compound, or molecule, having both a negatively charged ion (anion) and a positively charged ion (cation). In some cases, the zwitterionic polymer can include a zwitterionic pendant group (also described as a side group). In some cases, the zwitterionic polymer can be formed from one or more monomers, wherein the monomer includes a zwitterionic group.

In some cases, a composite material can have a polymer coating that includes polymerized units of a monomer including a zwitterionic group when the polymer coating is exposed to an aqueous environment, in particular blood, at a PH of about 7.4. In some cases, a zwitterionic group of a monomer can be formed by a carboxylic acid group, a sulfonic acid group, or a phosphoric acid group. In some cases, a monomer can include a zwitterionic group composed of an acrylate, a methacrylate, an acrylamide, or a methacrylamide. In some cases, a cation of a zwitterionic group can be formed by an (cyclo)aliphatic or aromatic amine, an amidine, or a guanidine. In some cases, a cation of a zwitterionic group can be a quaternary amine.

In some cases, a cation and an anion of a zwitterionic group can be part of the same pendant group of the monomer unit. In some cases, the pendant group has the structure formula: X—(CH2)n-N+R2-(CH2)m-Y or X—(CH2)n-O—P(O—)—(CH2)m-Z, wherein:

X is the point of covalent attachment to the repeat unit of the monomer;

each R is independently selected from C1- to C4-alkyl, in particular methyl;

n and m are each integers between 1 and 8;

Y is a anionic group selected from COO—, SO3-, SO3-, O—PO3-, and PO3-; and

Z is a cationic group derived from a (cyclo)aliphatic or aromatic amine, an amidine, a guanidine, or a quaternary amine, in particular NR'3+, wherein each R' is independently selected from C1- to C4-alkyl, in particular methyl.

Zwitterionic polymers can generally minimize or prevent biological responses normally caused by synthetic materials implanted in a body by creating a water-saturated surface that generally inhibits protein adsorption. Benefits of using zwitterionic polymeric surfaces include increasing the hydrophilicity, nonspecific protein adsorption resistance and/or platelet adhesion resistance of synthetic surfacesIn some cases, the composite material can be coated with a hydrogel to increase hydrophilicity of the leaflet surface. Increasing the hydrophilicity of the leaflet surface can be desirable for the reasons discussed herein.

Figure 6:
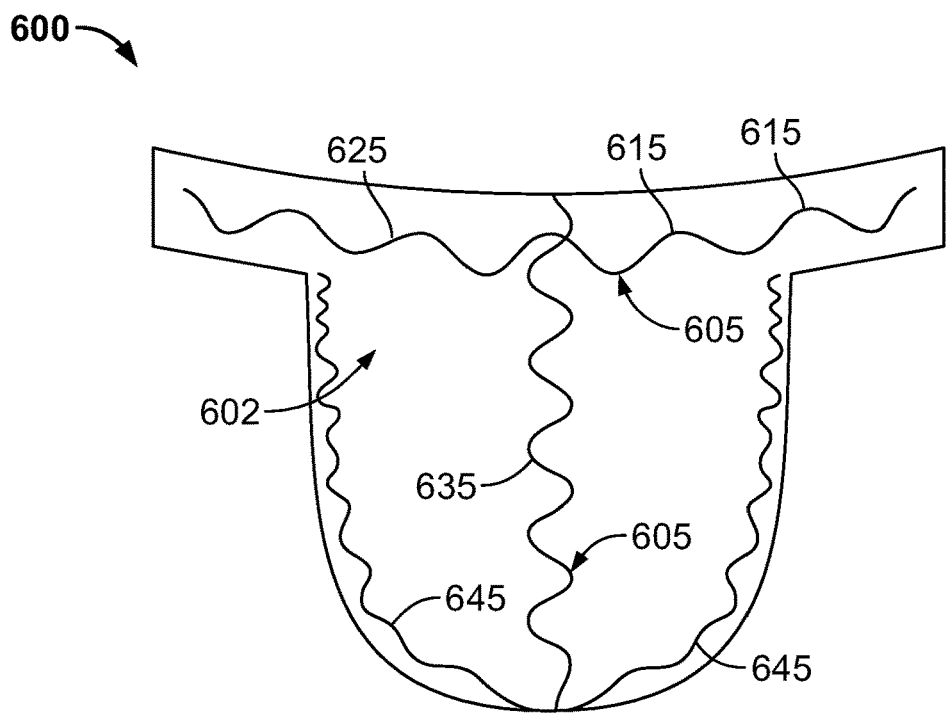

FIG. 6 shows another exemplary leaflet 600 of a prosthetic heart tissue valve provided herein. Leaflet 600 can be made of a composite material that includes a plurality of fibers 605 embedded in a polymer matrix 602. Each fiber 605 can have an extending direction and a plurality of undulations 615 orthogonal to the extending direction. As shown in FIG. 6, at least a portion of the plurality of fibers extends in a circumferential direction, a radial direction and a direction along at least a portion of an edge profile of leaflet. Leaflet 600 of FIG. 6 has circumferentially-directed fibers 625 that extend from one side edge to the opposite side edge of a sleeve portion and radially-directed fibers 635 that extend from a free edge to a bottom edge of the leaflet 600. Furthermore, as shown, leaflet 600 has at least one curved fiber, or a curvilinear fiber 645, that begins at one side edge of a leaflet belly region and ends at an opposite side edge, extending along a U-shape contour therebetween. In some cases, leaflet 600 can have curvilinear fibers 645 in the body portion and/or sleeve portion. In some cases, the curvilinear fibers 645 are shaped similar to an outline edge of the leaflet 600, for example, curvilinear fibers 645 extending along the U-shape contour. In some cases, the curvilinear fibers 645 can be shaped to a form or contour to provide non-linear elasticity to a particular area of the leaflet 600.

Still referring to FIG. 6, the curvilinear fiber 645 of leaflet 600 has a plurality of undulations 615 that vary in amplitude and wavelength. In particular, as shown in FIG. 6, the amplitude and wavelength of the undulations 615 of curvilinear fiber 645 gradually increase from the side edges proximate the sleeve portions to the apex of the leaflet belly region. In some cases, leaflet 600 can have at least one fiber 645 having a plurality of undulations 615 that vary in amplitude and/or the wavelength. In some cases, at least one fiber 645 can have a plurality of undulations 615 in at least one portion of the fiber, and no undulations in another portion of the fiber. In some cases, a fiber 645 of leaflet 600 can have a plurality of undulations 615 having a constant amplitude and wavelength.

Figure 7:
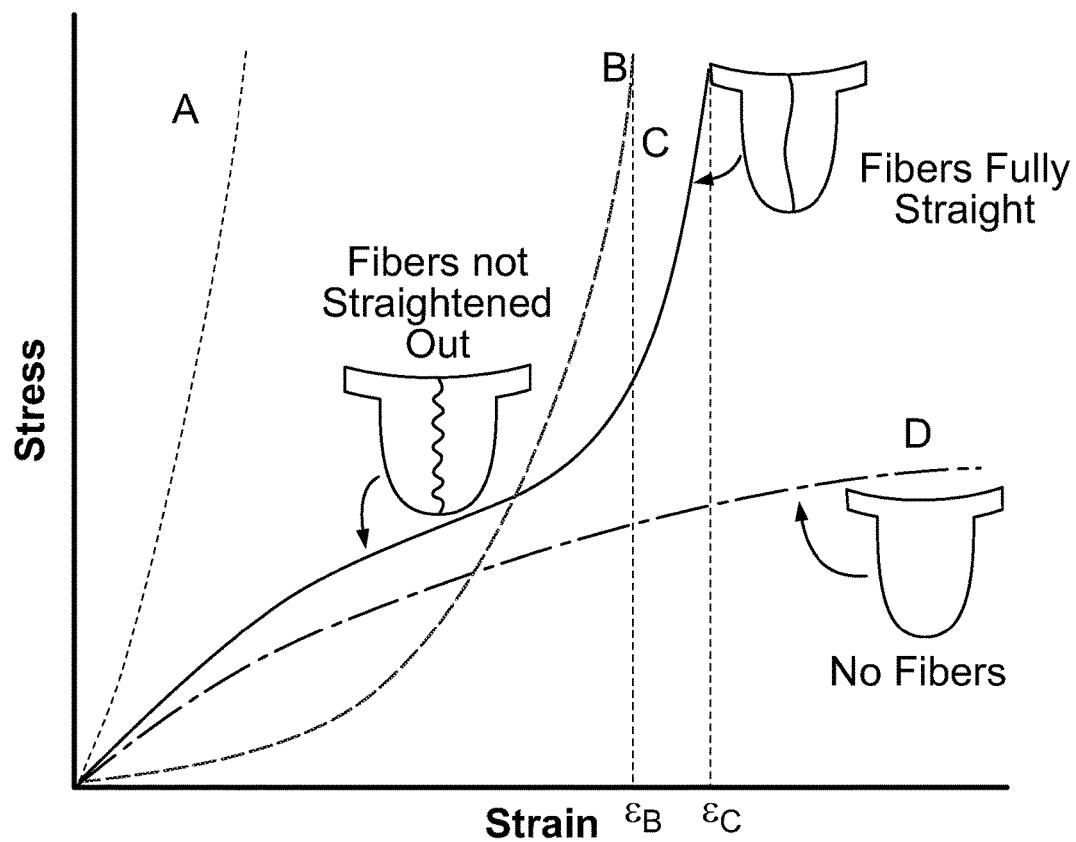
FIG. 7 shows a stress-strain graph of leaflets made of various materials.

FIG. 7 provides approximated stress-strain curves of leaflets made from various materials within an elastic region of deformation. More specifically, FIG. 7 provides a comparison of mechanical properties of a thermoplastic polymer A, bioprosthetic tissue B, a composite material provided herein C, and a pure elastomer D during elastic deformation. The composite material C being represented in the graph is composed of a composite material provided herein having an elastomeric material and a plurality of undulating fibers.

The stress-strain curve of FIG. 7 shows that the thermoplastic material A has a generally linear curve with a low elongation and a high yield strength as compared to the pure elastomer D that has an exponential curve having a high elongation and a low yield strength. The composite material C, as shown, has mechanical properties that are distinguishable from the thermoplastic polymer A and the pure elastomer D. In comparison to these materials, the composite material C has a higher elongation than thermoplastic A and a higher yield strength than elastomer D. However, the composite material C of FIG. 7 can behave like these materials at certain stages of elongation, depending on the fiber configuration within the composite material. For instance, the composite material C of FIG. 7 may behave similar to an elastomer D while the plurality of undulations of the fibers are initially stretching and behave similar to a thermoplastic A once the undulations of fibers have stretched and the fibers have become straight.

Still referring to FIG. 7, the composite material C, as a whole, behaves most like the bioprosthetic tissue B. As shown, both the bioprosthetic tissue B and composite material C are able to elongate to a comparable elongation length ($\varepsilon_B \sim \varepsilon_C$) in an elastic region of deformation. Also, the bioprosthetic tissue B and composite material C both exhibit a high yield strength when at a higher elongation value as compared to the thermoplastic A. The composite material C may, however, in some cases, exhibit higher stress values than the bioprosthetic tissue B at a low elongation range due to the elastomeric characteristics of its polymer matrix.

FIG. 7 provides an illustration of the mechanical characteristics of some embodiments of a composite material used to form tissue leaflets provided herein. The mechanical behavior of the composite material can, however, be modified by altering undulation characteristics of the fibers. Various configurations or orientations of the fibers can be applied to obtain suitable mechanical characteristics of the composite material can be modified. In some cases, elasticity of the composite material can be modified by changing wavelength, frequency and/or amplitude of a plurality of undulations of one or more fibers. For example, the elasticity of the composite material can be reduced, in some cases, by reducing the wavelengths and increasing the frequency of the fiber undulations.

Figure 8:
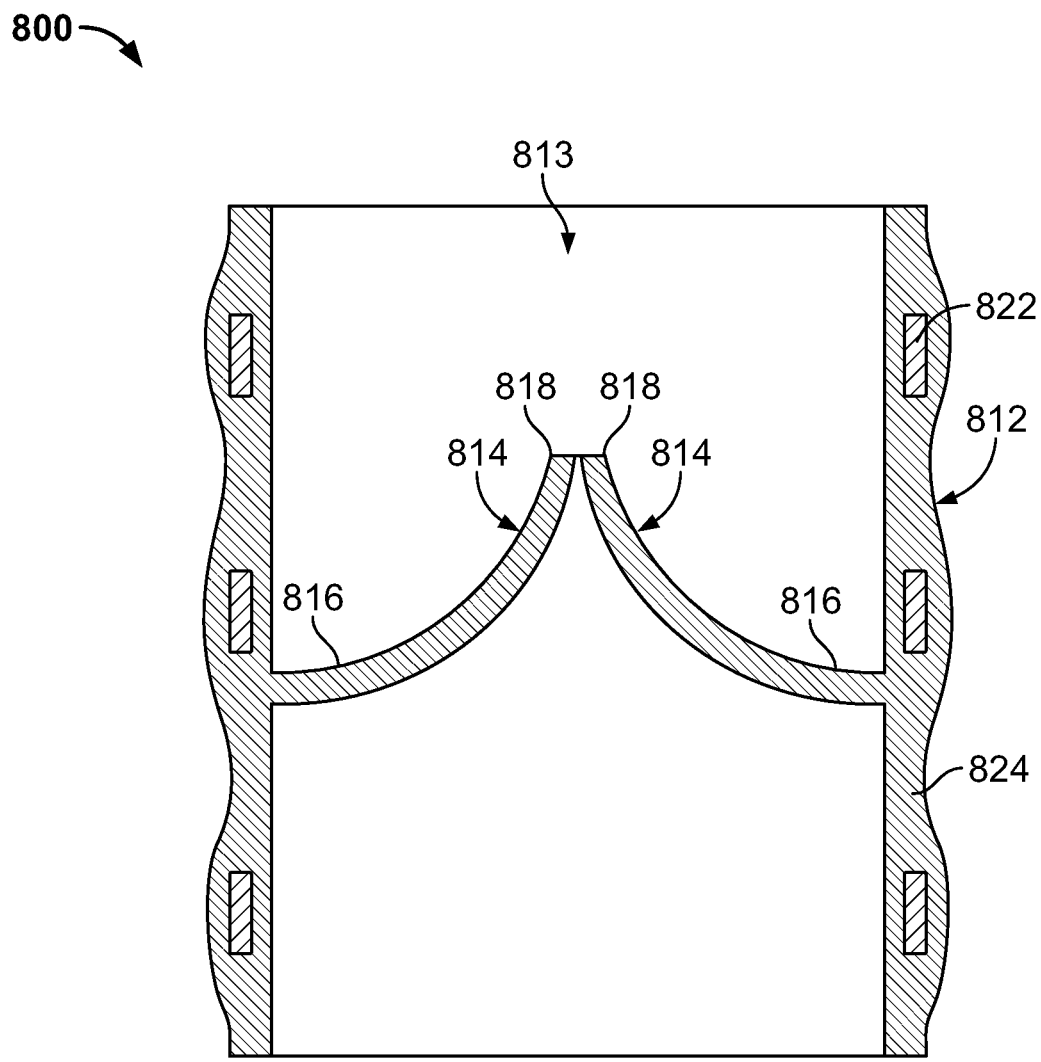
FIG. 8 is a side view of another exemplary prosthetic heart valve provided herein.

FIG. 8 provides another embodiment of an artificial heart valve 800. Prosthetic heart valve 800 includes a base 812 defining a substantially cylindrical passage 813 and a plurality of polymeric leaflets 814 disposed along the substantially cylindrical passage 813. Each polymeric leaflet 814 includes a respective root portion 816 coupled to base 812 and a respective edge portion 818 movable relative to the root portion 816 to coapt with the edge portions of the other polymeric leaflets along a coaptation region. In some cases, the each polymeric leaflet 814 includes a plurality of fibers. In some cases, the plurality of fibers 814 include a plurality of undulations to provide the leaflet with multi-stage elastic properties.

Base 812 includes a frame 822 disposed in a polymer layer 824. The polymer layer 824 can include plurality of fibers 814 that optionally include a plurality of undulations. Polymer layer 824 secures respective root portions 816 of polymeric leaflets 814 to the base 812. Polymer layer 824 can form a substantially continuous surface with respective root portions 816 of polymeric leaflets 814. This can reduce the likelihood of stress concentrations at the junction of respective root portions 816 and base 812. Additionally or alternatively, polymer layer 824 can be disposed between each of polymeric leaflets 814 and frame 822 such that polymer layer 824 protects polymeric leaflets 814 from inadvertent contact with frame 822 (e.g., as can occur through eccentric deformation of prosthetic heart valve 800 on a calcium deposit present at the implantation site).

In some cases, frame 822 is substantially cylindrical such that the outer surface of the base 812 is substantially cylindrical and the polymer layer 824 disposed on the frame 822 forms the substantially cylindrical passage 813. In some cases, frame 822 is completely disposed in the polymer layer 824, with the polymer layer 824 forming a contoured outer surface of the valve 800. In some cases, the frame 822 is partially disposed in the polymer layer 824. In some cases, the polymer layer 824 is applied to the frame 822 to form a substantially smooth inner and/or outer surface of the valve 800.

Methods provided herein can be used to form a medical device, such as a prosthetic heart valve leaflet provided herein, made of one or more composite materials. In particular, the methods provided herein can be used to form a leaflet with at least one of the composite materials provided herein having multi-stage elastic properties. In some cases, the method of forming a leaflet includes disposing a first polymeric layer on a mandrel. In some cases, the method of forming a leaflet includes disposing a plurality of fibers having a plurality of undulations on the first polymeric layer discussed herein. In some cases, the method of forming a leaflet includes disposing a second polymeric layer on the plurality of fibers discussed herein.

Various methods can be used for incorporating fibers into a polymer matrix to adequately bond fibers within a polymer matrix. Methods provided herein can be used to clean and/or surface modify fibers, encapsulate fibers in a jacket (e.g., a polymer jacket), deposit fibers into a mesh pattern of a leaflet, and coat a fibrous matrix with a polymer solution.

Fibers can be cleaned and/or surface modified to enhance adhesion of the fibers to another polymeric material, e.g. a polymer matrix or polymeric jacket. Suitable methods for cleaning and/or surface modifying fibers include, but are not limited to, atmospheric plasma treating, corona treating, acid etching and vacuum plasma treating. Cleaning and surface modification processes can be applied to fibers before or after the fibers have been configured onto a target surface.

Various methods can be employed to form fibers of a leaflet that are well known to those skilled in the art. In some cases, fibers can be made using solvent-based methods, such as extrusion or micro-capillary methods, as well as other methods, known to those skilled in the art. Examples of some suitable methods can include, but are not limited to, electrospinning, force spinning and melt-blowing processes. Electrospinning is a process that uses electrical charge to create fibers from a liquid while force spinning is a process that uses centrifugal force to create fibers. Melt-blowing is a process in which a molten thermoplastic resin is extruded through a die and then stretched and cooled with high-velocity air to form long, fine fibers.

In some cases, fibers can be formed prior to being deposited onto a leaflet. In particular, preformed fibers can be deposited and oriented as desired into a mesh pattern in the shape of a valve leaflet. Fibers can be oriented to optimize mechanical property anisotropy and allow for different degrees of elongation in different directions, if desired. In some cases, fibers can be deposited directly onto a target surface, e.g., a polymer matrix surface. Fibers can be deposited onto a target surface using methods provided herein to create a non-woven matrix or a woven fibrous matrix.

Individual fibers of a composite material can be optionally encapsulated in a jacket (e.g., a polymer jacket) to promote bonding and reduce the risk of fibers being released from a polymer matrix. In some cases, individual fibers can be encapsulated in a polymer jacket with a conformal coating by using a solution process, such as spray coating or dip coating. In some cases, fiber encapsulation can be facilitated using a reactive process to promote covalent bonding between a fiber and a polymer jacket. An exemplary reactive process can include coating a fiber with a primer solution of diisocyanate, such as monomers or low molecular weight oligomers of methylene diphenyl diisocyanate (MDI), curing the diisocyanate to the fiber surface, and applying over the coated fiber a reactive layer of hydroxyl terminated oligomer or amine terminated oligomers. In some cases, the reactive layer of hydroxyl terminated oligomer or amine terminated oligomers can be applied to a fiber without adding a diisocyanate coating.

Fibers can be encapsulated in a jacket (e.g., a polymer jacket) before or after being deposited onto the target surface. In the latter case, fibers can be coated with a polymer solution once formed and oriented as desired on a target surface. The polymer solution applied to the fibers can be a reactive or a non-reactive polymer solution. Residual solvents that might be present in the resultant polymer coated fiber can be minimized or removed by using appropriate solvents, heating, filtering and/or drying the composite material.

A number of embodiments of devices, systems, and methods have been provided herein. Nevertheless, it will be understood that various modifications may be made without departing from the spirit and scope of the subject matter provided herein. Accordingly, other embodiments are within the scope of the following claims.

What is claimed is:

1. A prosthetic heart valve comprising:
 a plurality of leaflets comprising:
   a composite material comprising a first plurality of polymeric fibers embedded in a polymer matrix, each fiber of the first plurality of polymeric fibers having a first common extending direction and a plurality of regularly spaced repeating undulations, wherein the plurality of regularly spaced repeating undulations of the first plurality of polymeric fibers is adapted to provide the composite material with multi-stage elastic properties; and
   wherein the plurality of regularly spaced repeating undulations of the first plurality of polymeric fibers has crests that extend in a direction orthogonal to the first common extending direction;
   wherein each leaflet comprises a first sleeve portion, a second sleeve portion, and a body portion disposed between the first and the second sleeve portions; and
   wherein at least a portion of the first plurality of polymeric fibers extend along a linear path along the first common extending direction comprising a circumferential direction between the first sleeve portion and the second sleeve portion.

2. The prosthetic heart valve of claim 1, wherein at least a portion of the first plurality of polymeric fibers extends along at least a portion of an edge contour of one or more of the plurality of leaflets of the prosthetic heart valve in the first common extending direction.

3. The prosthetic heart valve of claim 1, wherein the plurality of regularly spaced repeating undulations of each fiber is adapted to straighten along the linear path when the composite material is stretched in the first common extending direction.

4. The prosthetic heart valve of claim 1, wherein the composite material is more elastic when the plurality of fibers have the plurality of regularly spaced repeating undulations and less elastic when at least a portion of the plurality of fibers has been stretched into straight fibers.

5. The prosthetic heart valve of claim 1, wherein the composite material has a first elasticity when an average segment distance of the plurality of fibers is less than an average total fiber length of the plurality of fibers and a second elasticity when the average segment distance of the plurality of fibers is equal to or greater than the average total fiber length of the plurality of fibers, wherein the first elasticity is greater than the second elasticity.

6. The prosthetic heart valve of claim 1, wherein the regularly spaced repeating undulations have a predetermined average amplitude and a predetermined average wavelength.

7. The prosthetic heart valve of claim 1, wherein the plurality of fibers comprise a thermoplastic polymer.

8. The prosthetic heart valve of claim 1, wherein the plurality of fibers comprise a liquid crystalline polymer.

9. The prosthetic heart valve of claim 1, wherein the polymer matrix comprises an elastomeric polymer.

10. The prosthetic heart valve of claim 1, further comprising a second plurality of fibers embedded in the polymer matrix, each fiber of the second plurality of fibers having a second common extending direction and a plurality of regularly spaced repeating undulations.

11. The prosthetic heart valve of claim 10, wherein the first common extending direction of the first plurality of fibers defines a first longitudinal axis and the second common extending direction of the second plurality of fibers defines a second longitudinal axis, wherein the first longitudinal axis is orthogonal to the second longitudinal axis.

* * * * *